United States Patent [19]

Takano et al.

[11] Patent Number: 4,985,571

[45] Date of Patent: Jan. 15, 1991

[54] 6-MEMBERED LACTONES USEFUL AS INTERMEDIATES FOR ANTILIPEMIC MEVALONIC ACID LACTONES

[75] Inventors: Seiichi Takano, 1-16-4, Kamo, Sendai-shi, Miyagi-ken; Yohichi Shimazaki, Sendai; Yoshinori Sekiguchi, Sendai; Kunio Ogasawara, Sendai, all of Japan

[73] Assignee: Seiichi Takano, Sendai, Japan

[21] Appl. No.: 404,204

[22] Filed: Sep. 7, 1989

[30] Foreign Application Priority Data

Oct. 1, 1988 [JP] Japan .................................. 63-248545

[51] Int. Cl.$^5$ ............................................ C07D 493/04
[52] U.S. Cl. .................................... 549/283; 549/215
[58] Field of Search ................................ 549/283, 215

[56] References Cited

U.S. PATENT DOCUMENTS 4,837,341  6/1989  Tessier et al. ........................ 529/283

OTHER PUBLICATIONS

Tetrahedron Letters, vol. 29, No. 11, pp. 1255-1258, 1988, Bruce D. Roth, et al., "Synthesis of a Chiral Synthon for the Lactone Portion of Compactin and Mevinolin".

Primary Examiner—Jane T. Fan

Attorney, Agent, or Firm—Oblon, Spivak, McClelland, Maier & Neustadt

[57] ABSTRACT

A compound of the formula:

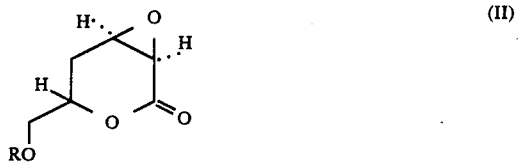

(II)

wherein R is an unsubstituted benzyl group, a p-nitrobenzyl group, a benzyl group in which the phenyl group is substituted by one or two substituents selected from the group consisting of $C_1$-$C_4$ alkyl groups and $C_1$-$C_4$ alkoxy groups, a phenyl group which is substituted by a $C_1$-$C_4$ alkylenedioxy group or by one or two substituents selected from the group consisting of $C_1$-$C_4$ alkyl groups and $C_1$-$C_4$ alkoxy groups, a $C_1$-$C_4$ trialkylsilyl group, a mono-substituted $C_1$-$C_4$ alkyldiarylsilyl group, a triarylmethyl group, a $C_1$-$C_4$ acyl group, a substituted or unsubstituted benzoyl group, a $C_1$-$C_4$ alkoxycarbonyl group, a substituted or unsubstituted aryloxycarbonyl group, a tetrahydropyranyl group, a benzyloxymethyl group, or a methoxymethyl group.

3 Claims, No Drawings

6-MEMBERED LACTONES USEFUL AS INTERMEDIATES FOR ANTILIPEMIC MEVALONIC ACID LACTONES

The present invention relates to novel compounds of the formula II useful as intermediates for antilipemic mevalonic acid lactones such as compactin and mevinolin and a process for their production, and a process for producing compounds of the formula III as identified hereinafter.

The present invention provides novel compounds of the formula II:

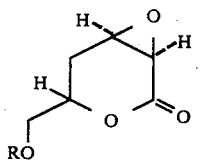

wherein R is an unsubstituted benzyl group, a p-nitrobenzyl group, a benzyl group in which the phenyl group is substituted by one or two substituents selected from the group consisting of $C_1$-$C_4$ alkyl groups and $C_1$-$C_4$ alkoxy groups, a phenyl group which is substituted by a $C_1$-$C_4$ alkylenedioxy group or by one or two substituents selected from the group consisting of $C_1$-$C_4$ alkyl groups and $C_1$-$C_4$ alkoxy groups, a $C_1$-$C_4$ trialkylsilyl group, a mono-substituted $C_1$-$C_4$ alkyldiarylsilyl group, a triarylmethyl group, a $C_1$-$C_4$ acyl group, a substituted or unsubstituted benzoyl group, a $C_1$-$C_4$ alkoxycarbonyl group, a substituted or unsubstituted aryloxycarbonyl group, a tetrahydropyranyl group, a benzyloxymethyl group, or a methoxymethyl group.

The compounds of the formula II can be synthesized by the following reaction scheme:

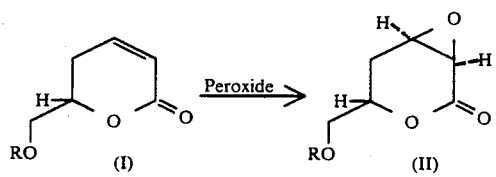

wherein R is as defined above.

The compounds of the formula II can be led to a compounds of the formula III which are useful as intermediates for antilipemic mevalonic acid lactones such as compactin and mevinolin:

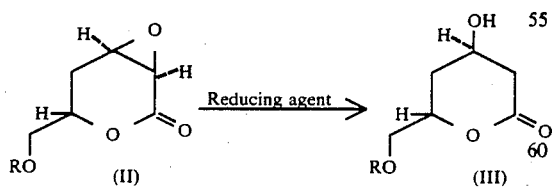

wherein R is as defined above.

The compounds of the formula III are useful, since they can readily be converted by a usual method to e.g. compounds of the following formula IV, whereby the mevalono lactone moiety can easily be connected to a carbon atom of other compound:

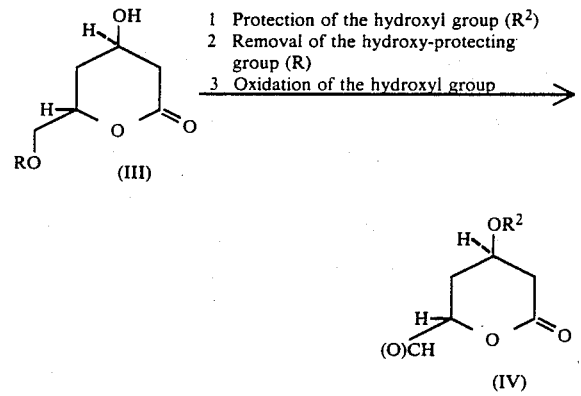

1 Protection of the hydroxyl group ($R^2$)
2 Removal of the hydroxy-protecting group (R)
3 Oxidation of the hydroxyl group wherein $R^2$ is an unsubstituted benzyl group, a p-nitrobenzyl group, a benzyl group in which the phenyl group is substituted by one or two substituents selected from the group consisting of $C_1$-$C_4$ alkyl groups and $C_1$-$C_4$ alkoxy groups, a phenyl group which is substituted by a $C_1$-$C_4$ alkylenedioxy group or by one or two substituents selected from the group consisting of $C_1$-$C_4$ alkyl groups and $C_1$-$C_4$ alkoxy groups, a $C_1$-$C_4$ trialkylsilyl group, a mono-substituted $C_1$-$C_4$ alkyldiarylsilyl group, a triarylmethyl group, a $C_1$-$C_4$ acyl group, a substituted or unsubstituted benzoyl group, a $C_1$-$C_4$ alkoxycarbonyl group, a substituted or unsubstituted aryloxycarbonyl group, a tetrahydropyranyl group, or a benzyloxymethyl group.

$R^2$ is preferably a group which will not be removed during the step of removing the hydroxy-protecting group R.

In the above definitions of R and $R^2$, the $C_1$-$C_4$ alkyl group includes methyl, ethyl, n-propyl, i-propyl, n-butyl, i-butyl and t-butyl, and the $C_1$-$C_4$ alkoxy group includes methoxy, ethoxy, n-propoxy, i-propoxy, n-butoxy, i-butoxy and t-butoxy.

As a preferred combination of $R^2$ and R, a combination may be mentioned wherein when R is a benzyl group, $R^2$ is a lower trialkylsilyl group such as a trimethylsilyl group or a triethylsilyl group.

Now, the reaction conditions for the process of the present invention will be described in detail.

The hydroxy-protecting group R is preferably a protecting group which will hardly be removed in any one of the reaction steps of the present invention.

As the benzyl group having hydrogen of its phenyl group substituted by a $C_1$-$C_4$ alkyl group or by a $C_1$-$C_4$ alkoxy group, a p-methylbenzyl group or a p-methoxybenzyl group may, for example, be mentioned.

The phenyl group which is substituted by one or two substituents selected from the group consisting of groups and $C_1$-$C_4$ groups includes, for example, a p-methoxyphenyl group and a 3,4-dimethoxyphenyl group. The phenyl group which is substituted by a $C_1$-$C_4$ alkylenedioxy group includes, for example, a 3,4-methylenedioxyphenyl group.

The $C_1$-$C_4$ trialkylsilyl group includes, for example, a trimethylsilyl group, a triethylsilyl group, a tri-n-propylsilyl group, a tri-i-propylsilyl group, a tri-n-butylsilyl group, a tri-i-butylsilyl group, a tri-t-butylsilyl group and a dimethyl-t-butylsilyl group.

The mono-substituted $C_1$-$C_4$ alkyl diarylsilyl group includes, for example, a diphenyl-t-butylsilyl group.

The triarylmethyl group includes, for example, a trityl group and a tris-(p-methoxyphenyl)methyl group.

As the $C_1$–$C_4$ acyl group, an acetyl group may, for example, be mentioned.

As the substituted or unsubstituted benzoyl group, a benzoyl group or a p-methoxybenzoyl group may be mentioned.

As the $C_1$–$C_4$ alkoxycarbonyl group, a methoxycarbonyl group may, for example, be mentioned.

As the substituted or unsubstituted aryloxycarbonyl group, a phenoxycarbonyl group or a p-nitrophenoxycarbonyl group may, for example, be mentioned.

Now, each reaction step will be described in detail.

Firstly, the reaction conditions for the production of the compound of the formula II from the compound of the formula I will be described.

As the peroxide, hydrogen peroxide, an aqueous hydrogen peroxide solution or an organic peroxide such as peracetic acid, perbenzoic acid, m-chloroperbenzoic acid, t-butylhydro peroxide or cumylhydro peroxide may be mentioned. As a preferred peroxide, hydrogen peroxide or an aqueous hydrogen peroxide solution may be mentioned. The molar ratio of the peroxide to the compound of the formula I is within a range of from 1.0 to 5.0 mol times, preferably from 1.0 to 2.0 mol times.

The pH during the oxidation is usually within a range of from 7.5 to 10.0, preferably from 7.5 to 8.5.

The reaction temperature is usually within a range of from 5° to 35° C., preferably from 10° to 25° C.

As the solvent, methanol, ethanol, n-propanol, dioxane or a mixture of two or more solvents selected from such solvents, may be used.

When hydrogen peroxide or an aqueous hydrogen peroxide solution is used, water may be used as the solvent or water may be used in combination with the above solvent.

Now, the conditions under which the compound of the formula III is produced from the compound of the formula II, will be described.

The molar ratio of the reducing agent to the compound of the formula II is usually within a range of from 1.0 to 5.0 mol times, preferably from 1.0 to 1.5 mol times.

The reaction temperature is preferably within a range of from 10° to 30° C.

As the reducing agent, (a) sodium phenyl seleno (trialkoxy) borate ($Na^+PhSeB(OR^1)^-$ wherein $R^1$ is methyl, ethyl, n-propyl or i-propyl), (b) aluminum amalgam (Al/Hg), (c) sodium iodide/sodium acetate (NaI/NaOCOCH$_3$), (d) sodium tellulium hydride (NaTeH), (e) samarium diiode (SmI$_2$), (f) zinc, (g) aromatic selenol such as selenophenol or (h) aromatic thiol such as thiophenol may be mentioned. As a preferred reducing agent, sodium phenyl seleno (trialkoxy) borate may be mentioned.

When the reducing agent (a), (b) or (d) is used, methanol, ethanol, n-propanol, i-propanol or a mixture of two or more such solvents, is preferably used as a solvent.

When the reducing agent (c) is used, it is preferred to use methanol, ethanol, n-propanol, i-propanol, acetone or a mixture of two or more such solvents.

When the reducing agent (e) is employed, it is preferred to use a solvent mixture of tetrahydrofuran with methanol, ethanol, n-propanol or i-propanol.

When the reducing agent (f) is used, acetic acid is preferably employed.

Now, the present invention will be described in further detail with reference to Reference Examples and Working Examples of the present invention. However, it should be understood that the present invention is by no means restricted by such specific Examples.

REFERENCE EXAMPLE 1

Preparation of (S)-5-benzyloxy-4-hydroxy-1-pentyne (the following compound)

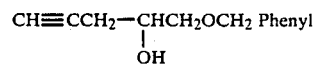

(For this process, Synthesis, 1987, 139 may be referred to.)

To a solution of 20.0 g (122 mmol) of (R)-O-benzylglycidol in dimethylsulfoxide (80 ml), 918.7 g (183 mmol) of a lithium acetylide-ethylenediamine complex (purity: 90%) was gradually added under stirring at a temperature of not higher than 5° C., and the mixture was stirred at the same temeprature for 40 minutes. To the reaction mixture, 150 ml of a saturated sodium chloride aqueous solution was added, and the mixture was acidified by an addition of concentrated hydrochloric acid. Then, the mixture was extracted with ethyl ether. The extract ether solution was washed with a 5% sodium bicarbonate aqueous solution and then with a saturated sodium chloride aqueous solution. The ether layer was dried over anhydrous magnesium sulfate, and the solvent was distilled off from the ether layer. After distilling off the solvent, the residue was purified by silica gel column chromatography to obtain 20.69 g (yield: 89%) of the above identified terminal acetylene compound. Boiling point: 95° C. (0.3 Torr).

REFERENCE EXAMPLE 2

Preparation of (S)-(Z)-6-benzyloxy-5-hydroxyhex-2-enoic acid lactone (compound of the formula I wherein R is benzyl)

(a) Preparation of the following compound ②

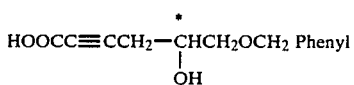

To a solution of 1.81 g (9.50 mmol) of the compound obtained in Reference Example 1 in 50 ml of tetrahydrofuran, 14.6 ml (22.8 mmol) of n-butyllithium (10% w/v in hexane) was added under stirring at −30° C.

The mixture was stirred at the same temperature for 15 minutes, then carbon dioxide gas was introduced, and the mixture was stirred for one hour. To the reaction mixture, 80 ml of a saturated sodium chloride aqueous solution was added, and the mixture was washed with ethyl ether. Then, the aqueous layer was acidified with concentrated hydrochloric acid and extracted with ethyl ether. The ethyl ether layer was dried over anhydrous magnesium sulfate. The solvent was distilled off to obtain 2.27 g of a crude product of the carboxylic acid ②.

(b) Preparation of the following compound (cis-form)

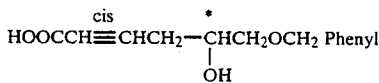

1.72 g out of 2.27 g of the crude carboxylic acid ② was partially hydrogenated in 30 ml of ethyl acetate in the presence of 100 mg of a Lindlar catalyst at room temperature (about 10°–30° C.) under atmospheric pressure for 8.5 hours. The reaction solution after the partial hydrogenation was subjected to filtration by celite, and then the solvent was distilled off to obtain 1.57 g of a crude product of (Z)-carboxylic acid ③

(c) Preparation of the above identified compound (compound of the formula I wherein R is benzyl)

1.10 g of the crude carboxylic acid was ③ was refluxed for 8.5 hours in 30 ml of benzene by means of a Dean-Stark apparatus. The benzene solution was washed with a 5% sodium bicarbonate aqueous solution and then with a saturated sodium chloride aqueous solution. The benzene layer was dried over anhydrous magnesium sulfate, and the solvent was distilled off. The residue was purified by silica gel column chromatography (developing solvent: ethyl ether/n-hexane=1/1) to obtain α,β-unsaturated-δ-lactone.

$[\alpha]_D^{27}: -115.07°$ (c=1.008, CHCl$_3$)

EXAMPLE 1

Preparation of lactone of (2R,3R,5S)-6-benzyloxy-2,3-epoxy-5-hydroxyhexanoic acid (compound of the formula II wherein R is benzyl)

To 20 ml of a methanol solution containing 855 mg (3.92 mmol) of the lactone (compound of the formula I wherein R is benzyl), 1.33 ml (2.35 mmol) of a 30% hydrogen peroxide aqueous solution and 0.39 ml (2.35 mmol) of a 6N sodium hydroxide aqueous solution were added at room temperature. After stirring at room temperature for 30 minutes, the reaction mixture was diluted with 50 ml of ethyl ether and 50 ml of water and then acidified by an addition of concentrated hydrochloric acid. The organic layer was separated, and the aqueous layer was extracted with 50 ml of methylene chloride. The extract was put together with the organic layer, and the mixture was washed twice with an aqueous sodium chloride solution and then dried over anhydrous magnesium sulfate. Then, the solvent was distilled off under reduced pressure. To the residue, 10 ml of benzene was added, and the mixture was refluxed under azeotropic dehydration for ring closure.

The solvent was distilled off under reduced pressure, and the residue was purified by silica gel chromatography (45 g) with ethyl ether/hexane (1/2 v/v) to obtain the above identified compound as a colorless oily substance. Amount: 671 mg (yield: 73%).

Boiling point: 190° C. (0.3 Torr)
[Kugelrohl distillation]
$[\alpha]_D^{24}: +48.24°$ (c=1.028, CHCl$_3$)
Elemental analysis (C$_{13}$H$_{14}$O$_4$, molecular weight: 234.25)
Calculated: C 66.66%, H 6.02%
Found: C 66.88%, H 6.11%
IR(Film): $\nu$=1740 cm$^{-1}$
$^1$H-MNR(CDCl$_3$/TMS):
$\delta$=2.30(m,2H), 3.60(m,3H), 3.69(m,1H), 4.58(s,2H), 4.70(m,1H), 7.34(s,5H)

EXAMPLE 2

Preparation of lactone of (3R,5S)-6-benzyloxy-3,5-dihydroxyhexanoic acid (compound of the formula III wherein R is benzyl)

To 10 ml of an isopropanol solution containing 1.12 g (3.6 mmol) of diphenyl diselenide, 273 mg (7.2 mmol) of sodium borohydride was gradually added at room temeprature. A few minutes after the completion of the addition, 0.07 ml of acetic acid was added thereto at room temperature.

Five minutes later, the mixture was cooled to 0° C., and 20 ml of an isopropanol solution containing 563 mg (2.4 mmol) of the epoxy lactone obtained in Example 1, was dropwise added thereto. The mixture was stirred at 0° C. for 30 minutes.

The reaction mixture was diluted with 50 ml of ethyl acetate, and the organic layer was washed with 50 ml of an aqueous sodium chloride solution and then dried over anhydrous magnesium sulfate. The solvent was distilled off under reduced pressure, and the residue was purified by silica gel chromatography (20 g) with ethyl ether/hexane (1/2 v/v) to obtain the above identified compound as a colorless oily substance. Amount: 397 mg (yield: 87%).

$[\alpha]_D^{29}: +6.59°$ (c=1.032, CHCl$_3$)

Elemental analysis (C$_{13}$H$_{16}$O$_4$, molecular weight: 236.27)
Calculated: C 66.08%, H 6.83%
Found: C 65.95%, H 6.96%
IR(Film): $\nu$=3400, 1720 cm$^{-1}$
$^1$H-MNR(CDCl$_3$/TMS):
$\delta$=1.95(m,2H), 2.30(s,1H,exchangeable with D$_2$O), 2.68(d,2H,J=4.15Hz), 3.68(dd,2H,J=4.15,1.8Hz), 4.45(m,1H), 4.58(s,2H), 4.86(m,1H), 7.35(s,5H)

The analytical values of the 3-acetoxy derivative of the compound of the formula III wherein R is benzyl, were as follows:
$^1$H-MNR(500MHz)(CDCl$_3$/TMS):
$\delta$=2.07(s,3H;CH$_3$CO), 2.09(m,2H,2×4H), 2.72(ddd,1H,J=17.0 (geminal),3.75(with3eqH), 2.0(with4eqH), Hz;2eqH), 2.78[dd,1H,J=17.0(geminal), 3.75(with3eqH);2axH], 3.63(dd,1H,J=12.0(geminal), 4.0Hz(with5azH);6H), 3.70(dd,1H,J=12.0(geminal), 3.75(with5azH);Hz6H), 4.56(d,1H,J=12.0Hz;benzylicH), 4.60(d,1H,J=12.0Hz,benzylicH), 4.71[d,quat,1H,J=10.0(with4axH), 3.75(with4eqH,6Hx2);5H], 5.32[quint,1H,3.75(with2eqH,2axH,4eqH,and 4axH);5H], 7.35(m,5H;aromatic protons):
MS (70 eV):m/Z=236 (M+), 91 (100%)

We claim:

1. A compound of the formula:

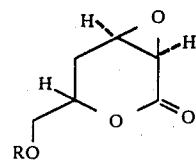

wherein R is an unsubstituted benzyl group, a p-nitrobenzyl group, a benzyl group in which the phenyl group is substituted by one or two substituents selected from the group consisting of C$_1$–C$_4$ alkyl groups and C$_1$–C$_4$ alkoxy groups, a phenyl group which is substituted by a $C_1$–$C_4$ alkylenedioxy group or by one or two substituents selected from the group consisting of $C_1$–$C_4$ alkyl groups and $C_1$–$C_4$ alkoxy groups, a $C_1$–$C_4$ trialkylsilyl group, a $C_1$–$C_4$ alkyldiarylsilyl group, a triarylmethyl group, a $C_1$–$C_4$ acyl group, a substituted or unsubstituted benzoyl group, a $C_1$–$C_4$ alkoxycarbonyl group, a substituted or unsubstituted aryloxycarbonyl group, a tetrahydropyranyl group, a benzyloxymethyl group, or a methoxymethyl group.

2. The compound according to claim 1, wherein R is an unsubstituted benzyl group, or a benzyl group having hydrogen of its phenyl group substituted by a $C_1$–$C_4$ alkyl group or by a $C_1$–$C_4$ alkoxy group.

3. The compound according to claim 1, wherein the triarylmethyl group is trityl or tris-(p-methoxyphenyl)-methyl, the substituted benzoyl group is p-methoxybenzoyl, the substituted aryloxycarbonyl group is p-nitrophenoxycarbonyl and the unsubstituted aryloxycarbonyl group is phenoxycarbonyl.

* * * * *